US00PP37607P2

(12) United States Plant Patent
Koning

(10) Patent No.: US PP37,607 P2
(45) Date of Patent: Aug. 18, 2026

(54) ***LAVANDULA* PLANT NAMED 'Felice Silver'**

(50) Latin Name: *Lavandula angustifolia*
Varietal Denomination: Felice Silver

(71) Applicant: L. KONING BEHEER B.V., Nuis (NL)

(72) Inventor: Lammert Koning, Nuis (NL)

(73) Assignee: L. KONING BEHEER B.V., Nais (NL)

( * ) Notice: Subject to any disclaimer, the term of this patent is extended or adjusted under 35 U.S.C. 154(b) by 0 days.

(21) Appl. No.: 19/399,201

(22) Filed: Nov. 24, 2025

(51) Int. Cl.
*A01H 5/02* (2018.01)
*A01H 6/50* (2018.01)

(52) U.S. Cl.
USPC ..... Plt./445

(58) Field of Classification Search
USPC ..... Plt./445
See application file for complete search history.

*Primary Examiner* — Susan Mccormick Ewoldt
(74) *Attorney, Agent, or Firm* — C. Anne Whealy

(57) ABSTRACT

A new and distinct cultivar of *Lavandula* plant named 'Felice Silver', characterized by its compact, broadly upright and uniformly mounded plant habit; freely branching growth habit; dense and bushy appearance; silvery green-colored leaves; freely flowering habit; violet-colored flowers positioned on strong and erect silvery green-colored peduncles; and good garden performance.

3 Drawing Sheets

Figure 1:
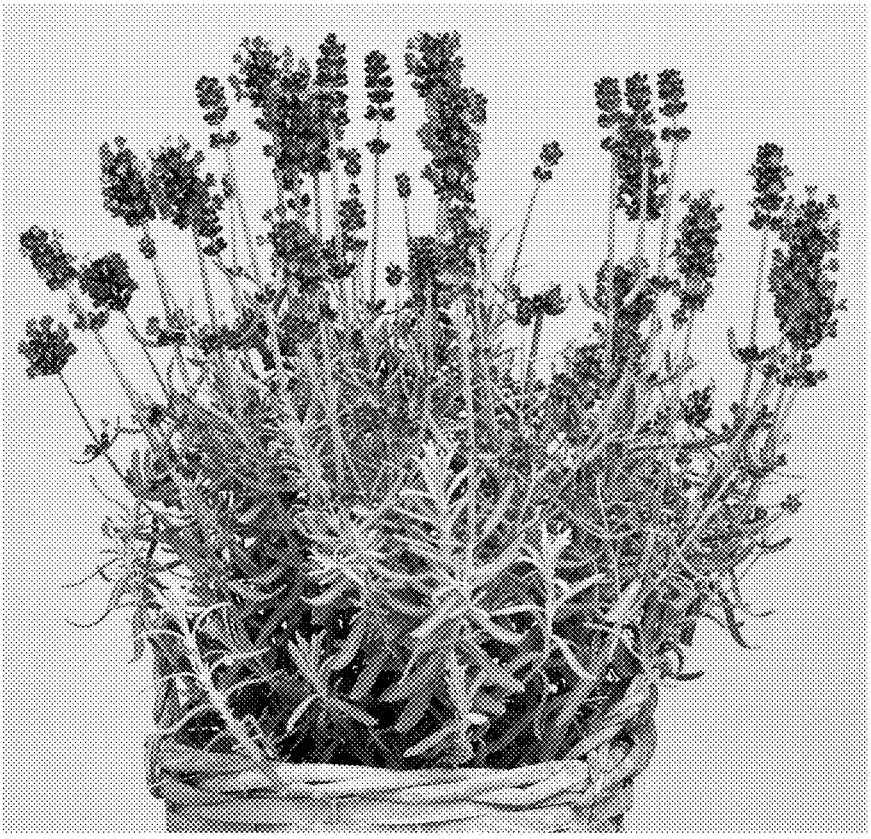

Botanical designation: *Lavandula angustifolia.*
Cultivar denomination: 'FELICE SILVER'.

CROSS-REFERENCED TO CLOSELY-RELATED APPLICATION

A European Community Plant Breeder's Rights application for the instant plant was filed by the Applicant/Assignee, L. Koning Beheer B. V. of Nuis, The Netherlands on Jul. 3, 2025, application number 2025/1468 and published on Oct. 15, 2025. Foreign priority is not claimed to this application.

BACKGROUND OF THE INVENTION

The present invention relates to a new and distinct *Lavandula* plant, botanically known as *Lavandula angustifolia*, commonly referred to as Lavender and hereinafter referred to by the name 'Felice Silver'.

The new *Lavandula* plant is a naturally-occurring branch mutation of *Lavandula angustifolia* 'Felice Purple', not patented. The new *Lavandula* plant was discovered and selected by the Inventor on a single flowering plant within a population of plants of 'Felice Purple' in a controlled environment in Boskoop, The Netherlands in May, 2024.

Asexual reproduction of the new *Lavandula* plant by terminal cuttings in a controlled greenhouse environment in Boskoop, The Netherlands since August, 2024 has shown that the unique features of this new *Lavandula* plant are stable and reproduced true to type in successive generations.

SUMMARY OF THE INVENTION

Plants of the new *Lavandula* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of the new *Lavandula* plant. These characteristics in combination distinguish 'Felice Silver' as a new and distinct *Lavandula* plant:

1. Compact, broadly upright and uniformly mounded plant habit.
2. Freely branching growth habit; dense and bushy appearance.
3. Silvery green-colored leaves.
4. Freely flowering habit.
5. Violet-colored flowers positioned on strong and erect silvery green-colored peduncles.
6. Good garden performance.

Plants of the new *Lavandula* differ primarily from plants of mutation parent, 'Felice Purple', primarily in leaf color as leaves of plants of the new *Lavandula* are silvery green in color whereas leaves of plants of 'Felice Purple' are medium green in color.

Plants of the new *Lavandula* can be compared to plants of the *Lavandula angustifolia* 'Annet', disclosed in U.S. Plant Pat. No. 28,867. In side-by-side comparisons, plants of the new *Lavandula* differ primarily from plants of 'Annet' in the following characteristics:

1. Plants of the new *Lavandula* are more compact than plants of 'Annet'.
2. Plants of the new *Lavandula* are denser than plants of 'Annet'.
3. Leaves of plants of the new *Lavandula* are silvery green in color whereas leaves of plants of 'Annet' are medium green in color.
4. Plants of the new *Lavandula* have darker violet-colored flowers than plants of 'Annet'.

Plants of the new *Lavandula* can also be compared to plants of the *Lavandula angustifolia* 'Blue Royalty', disclosed in U.S. Plant Pat. No. 20,657. In side-by-side comparisons, plants of the new *Lavandula* differ primarily from plants of 'Blue Royalty' in the following characteristics:

1. Plants of the new *Lavandula* are more compact than plants of 'Blue Royalty'.
2. Plants of the new *Lavandula* are denser than plants of 'Blue Royalty'.
3. Leaves of plants of the new *Lavandula* are silvery green in color whereas leaves of plants of 'Blue Royalty' are medium to dark green in color.
4. Plants of the new *Lavandula* have darker violet-colored flowers than plants of 'Blue Royalty'.

BRIEF DESCRIPTION OF THE PHOTOGRAPHS

The accompanying photographs illustrate the overall appearance of the new *Lavandula* plant showing the colors as true as it is reasonably possible to obtain in colored reproductions of this type. Colors in the photographs may differ slightly from the color values cited in the detailed botanical description which accurately describe the colors of the new *Lavandula* plant.

The photograph on the first sheet (FIG. 1) is a side perspective view of a typical flowering plant of 'Felice Silver' grown in a container.

Figure 2:
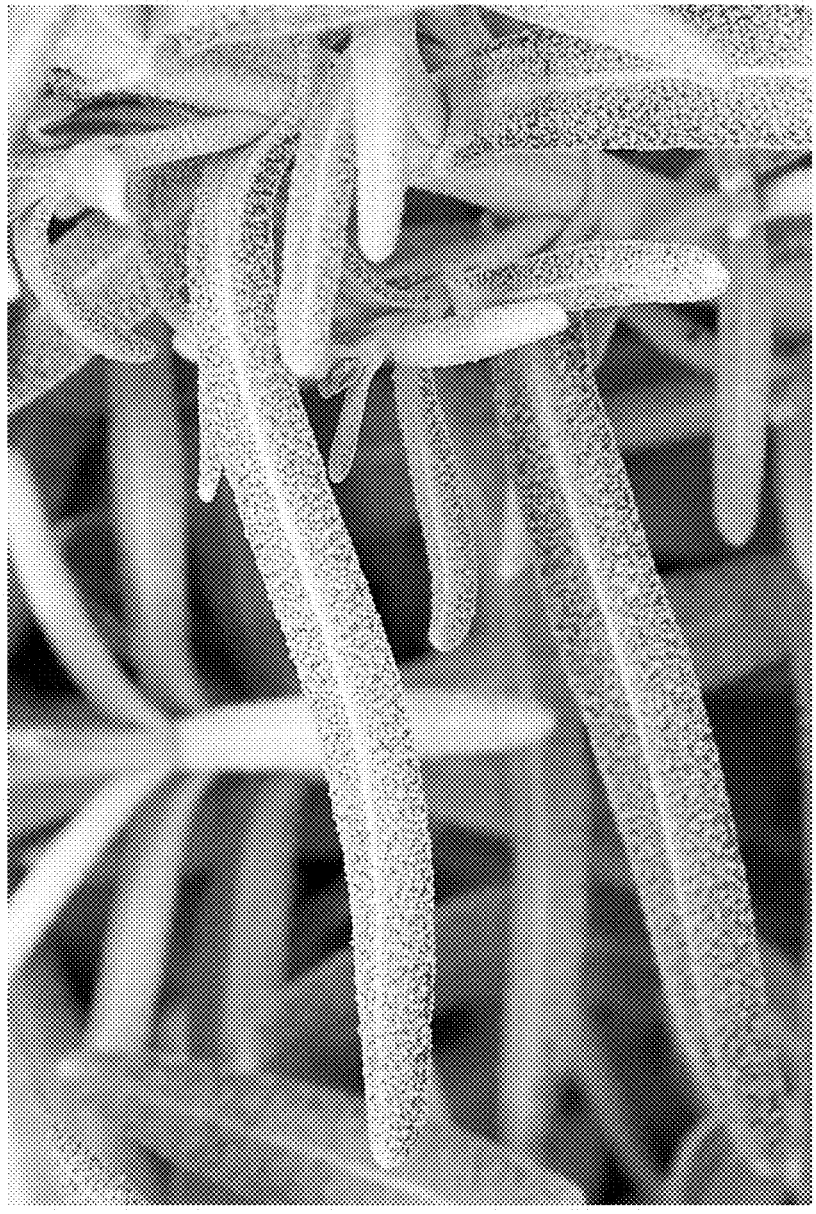

The photograph on the second sheet (FIG. 2) is a close-up view of typical leaves of 'Felice Silver'.

Figure 3:
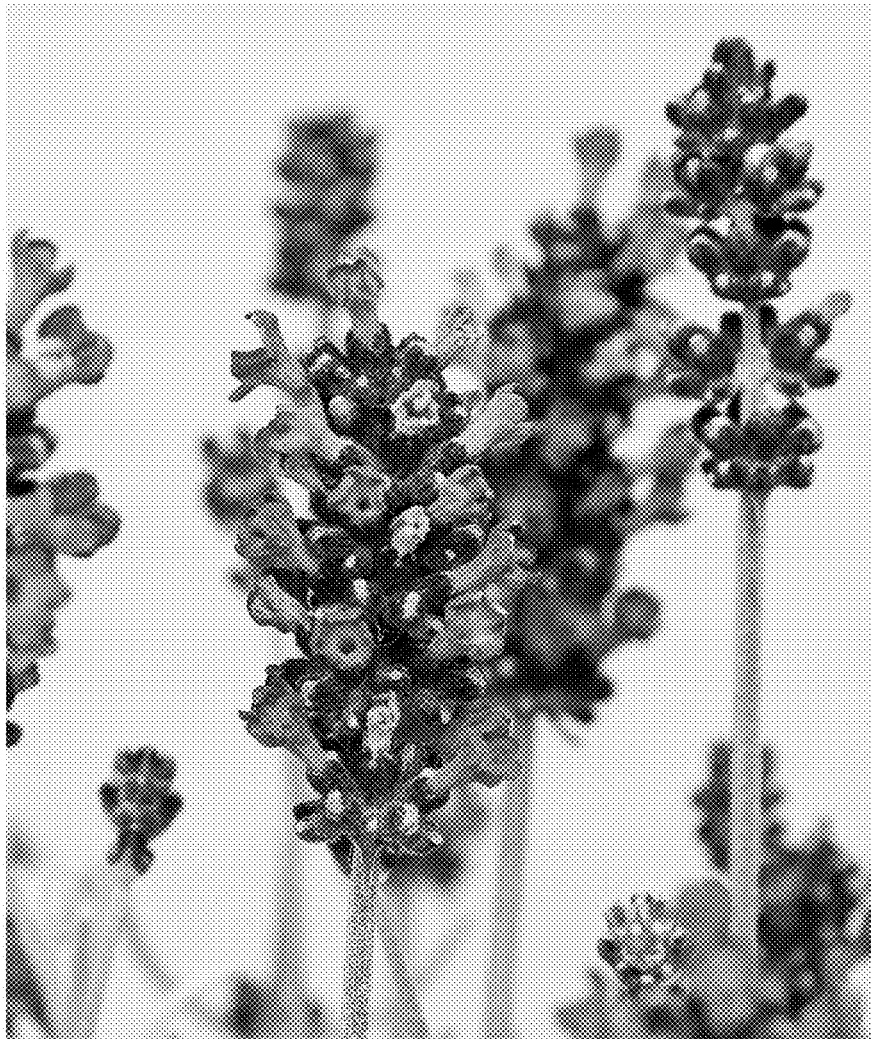

The photograph on the third sheet (FIG. 3) is a close-up view of a typical inflorescences of 'Felice Silver'.

DETAILED BOTANICAL DESCRIPTION

Plants used in the aforementioned photographs and following detailed description were grown in 14-cm containers during the summer in a glass-covered greenhouse in Boskoop, The Netherlands and under cultural practices typical of commercial *Lavandula* production. Plants were twelve months old when the photographs and description were taken. During the production of the plants, day temperatures ranged from 18° C. to 25° C. and night temperatures ranged from 15° C. to 18° C. In the following description, color references are made to The Royal Horticultural Society Colour Chart, Sixth Edition 2019 reprint, except where general terms of ordinary dictionary significance are used.

Botanical classification: *Lavandula angustifolia* 'Felice Silver'.

Parentage: Naturally-occurring branch mutation of *Lavandula angustifolia* 'Felice Purple', not patented.

Propagation:

*Type*.—Terminal vegetative cuttings.

*Time to initiate roots, summer and winter*.—About ten days at temperatures about 18° C.

*Time to produce a rooted young plant, summer*.—About 60 days at temperatures about 20° C.

*Time to produce a rooted young plant, winter*.—About 70 days at temperatures about 20° C.

*Root description*.—Fine, fibrous; initially white in color and becoming more brown with development; actual color of the roots is dependent on substrate composition, water quality, fertilizer type and formulation.

*Rooting habit*.—Freely branching; dense.

Plant description:

*Plant and growth habit*.—Herbaceous perennial; compact, broadly upright and uniformly mounding plant habit; broadly obovate in overall plant shape; freely branching habit; moderately vigorous to vigorous growth habit and moderate growth rate; flowers arranged in verticillasters on crowded spikes.

*Plant height, soil level to top of foliar plane*.—About 21.4 cm.

*Plant height, soil level to top of floral plane*.—About 28.4 cm.

*Plant width*.—About 30.2 cm.

*Lateral branch description*.—Quantity per plant: About three primary lateral branches and about 38 secondary lateral branches developing per plant; pinching enhances branching potential. Length: About 9.4 cm. Diameter: About 2 mm. Internode length: About 1 cm. Strength: Moderately strong; flexible. Aspect: Upright to about 30° from vertical. Texture and luster: Densely tomentose; matte. Color, when developing: Close to 193D. Color, developed: Close to a blend of 148A to 148C and 191A; at the internodes, close to 191B; if woody, close to 199D.

*Leaf description*.—Arrangement: Opposite, simple; sessile. Quantity per lateral branch: About 20. Length: About 3 cm. Width: About 5 mm. Shape: Narrowly oblanceolate; moderately carinate. Apex: Bluntly acute to obtuse. Base: Broadly cuneate. Margin: Entire; slightly to moderately revolute; not lobed. Texture and luster, upper and lower surfaces: Densely tomentose; matte. Fragrance: Strongly aromatic, pungent. Venation pattern: Pinnate. Color: Developing leaves, upper surface: Close to 191B; venation, close to 191B. Developing leaves, lower surface: Close to 191B; venation, close to 192C. Fully expanded leaves, upper surface: Close to 189A; venation, close to 189A. Fully expanded leaves, lower surface: Close to 191A; venation, close to 191B.

Flower description:

*Flower type, arrangement and habit*.—Small single salverform flowers arranged in compact verticillasters on crowded terminal spikes; freely flowering, about 95 flowers developing per inflorescence and more than 4,850 flowers developing per plant; flowers with a two-lobed upper lip and a three-lobed lower lip; flowers face mostly outwardly on the spike.

*Natural flowering season*.—Long flowering period; continuous from late spring into the late summer in The Netherlands; plants reblooming.

*Flower longevity on the plant*.—Individual flowers last about four weeks on the plant depending on environmental conditions; flowers not persistent.

*Fragrance*.—None detected.

*Flower buds*.—Length: About 5 mm. Diameter: About 3 mm. Shape: Oblong to obovate. Texture and luster: Densely tomentose; matte. Color: Close to 86A.

*Inflorescence height*.—About 3.7 cm.

*Inflorescence diameter*.—About 2.1 cm.

*Flower size*.—Diameter: About 5 mm. Depth (height): About 1.1 cm. Throat diameter: About 1 mm. Tube length: About 7 mm. Tube diameter: About 2 mm.

*Petals*.—Quantity and arrangement: Upper lip, two-lobed and lower lip, three-lobed. Length, upper lip: About 1 cm. Width, upper lip: About 3 mm. Length, lower lip: About 9 mm. Width, lower lip: About 2 mm. Shape, upper lip: Spatulate; lower 70% fused into a tube. Shape, lower lip: Spatulate; lower 80% fused into a tube. Apex, upper and lower lips: Obtuse. Margin, upper and lower lips, free parts: Entire; moderately undulate. Texture and luster, upper and lower lips, upper and lower surfaces: Smooth, glabrous; moderately velvety; matte. Color, upper and lower lips: When opening, upper and lower surfaces: Close to N88B. Fully opened, upper surface: Close to N88C; axial stripes, close to N88A. Fully opened, lower surface: Close to 86C. Throat: Distally, close to N88C; proximally, close to NN155D. Tube: Distally, close to 86C; proximally, close to NN155D.

*Basal flower bracts*.—Quantity and arrangement: Each group of five to seven flowers is subtended by a single basal flower bract. Length: About 3 mm. Width: About 3 mm. Shape: Rhomboidal. Apex: Narrowly apiculate. Base: Cuneate. Margin: Finely dentate. Texture and luster, upper and lower surfaces: Mostly smooth, glabrous with sparse tomentose pubescence along marginal edges; slightly glossy. Color, upper and lower surfaces: Close to N199B; marginal edges, close to N155D.

*Sepals*.—Quantity and arrangement: Five, fused into a campanulate tube. Calyx length: About 5 mm. Calyx diameter: About 3 mm. Length: About 5 mm. Width: About 1.5 mm. Shape: Linear. Apex: Broadly acute. Margin: Entire. Texture and luster, upper surface: Smooth, glabrous; matte. Texture and luster, lower surface: Densely pubescent; matte. Color: When opening and fully opened, upper surface: Close to 144C; venation, close to 147A. When opening and fully opened, lower surface: Close to 86A; towards the base, close to 195C.

*Peduncles*.—Length: About 8.7 cm. Diameter: About 2 mm. Aspect: Mostly upright. Strength: Strong; flexible. Texture and luster: Moderately to densely tomentose; matte. Color: Close to 189A.

*Pedicels*.—Length: About 1 mm. Diameter: About 1 mm. Aspect: About 45° to 115° from peduncle axis. Strength: Moderately strong; flexible. Texture and luster: Densely tomentose; matte. Color: Close to 191D.

*Reproductive organs*.—Stamens: Quantity per flower: Four. Filament length: About 1.5 mm. Filament color: Close to NN155C. Anther shape: Short reniform; dorsifixed. Anther size: About 0.5 mm by 0.5 mm. Anther color: Close to 203A. Pollen amount: Moderate. Pollen color: Close to N25D. Pistils: Quantity per flower: One. Pistil length: About 5.5 mm. Stigma shape: Club-shaped. Stigma diameter: About 0.5 mm. Stigma color: Close to 86B. Style length: About 4.5 mm. Style color: Close to NN155B. Ovary color: Close to 146B and 146C.

*Seeds and fruits*.—To date, seed and fruit production has not been observed on plants of the new *Lavandula*.

Pathogen & pest resistance: To date, plants of the new *Lavandula* have not been noted to be resistant to pathogens and pests common to *Lavandula* plants.

Garden performance: Plants of the new *Lavandula* have exhibited good tolerance to rain and wind and have been observed to tolerate temperatures from about −17° C. to about 40° C. Plants of the new *Lavandula* are suitable for USDA Hardiness Zones 6 to 10.

It is claimed:

1. A new and distinct *Lavandula* plant named 'Felice Silver' as herein illustrated and described.

* * * * *